(12) United States Patent
Nagel et al.

(10) Patent No.: US 11,400,285 B2
(45) Date of Patent: Aug. 2, 2022

(54) METHODS AND SYSTEMS FOR TREMOR REDUCTION

(71) Applicant: Universidad Adolfo Ibañez, Santiago (CL)

(72) Inventors: Felipe Nagel, Viña del Mar (CL);
Federico Jensen, Viña del Mar (CL);
Alex Cariman, Viña del Mar (CL);
Cedric Little, Viña del Mar (CL)

(73) Assignee: Universidad Adolfo Ibañez, Santiago (CL)

( * ) Notice: Subject to any disclaimer, the term of this patent is extended or adjusted under 35 U.S.C. 154(b) by 6 days.

(21) Appl. No.: 16/446,612

(22) Filed: Jun. 19, 2019

(65) Prior Publication Data

US 2019/0298996 A1 Oct. 3, 2019

Related U.S. Application Data

(62) Division of application No. 15/080,583, filed on Mar. 25, 2016, now Pat. No. 10,363,413.

(51) Int. Cl.
*A61N 1/36* (2006.01)
*A61B 5/11* (2006.01)
(Continued)

(52) U.S. Cl.
CPC ........ *A61N 1/36003* (2013.01); *A61B 5/0004* (2013.01); *A61B 5/1101* (2013.01);
(Continued)

(58) Field of Classification Search
CPC ............ A61N 1/36003; A61N 1/36031; A61N 1/025; A61N 1/08; A61N 1/36034; A61B 5/389; A61B 5/0004; A61B 5/1101; A61B 5/4836; A61B 5/6824; A61B 5/7214; A61B 5/725; A61B 5/6832; A61B 2560/0204; A61B 2562/0219; A61B 2562/04
(Continued)

(56) References Cited

U.S. PATENT DOCUMENTS 9,272,139 B2 3/2016 Hamilton et al.
2004/0088025 A1 5/2004 Gesotti
(Continued)

FOREIGN PATENT DOCUMENTS

WO 2014113813 A1 7/2014

OTHER PUBLICATIONS

International Search Report for PCT/IB2017/000415 dated Aug. 1, 2017.
Thenganatt et al. "Distinguishing Essential Tremor from Parkinson's Disease: Bedside Tests and Laboratory Evaluations," Expert Rev. Neurother. Jun. 2012; 12(6): 687-696. dol: 10. 1586/ern.12.49.

*Primary Examiner* — Erin M Piateski
(74) *Attorney, Agent, or Firm* — McDonnell Boehnen Hulbert & Bergnoff LLP

(57) ABSTRACT

A tremor-reduction system is provided that delivers electric current to a body region of a subject that is associated with a tremor. A computing device stores received data associated with a tremulous movement of the body region and determines measurements associated with the stored data. If a magnitude of the most recent tremulous movement is the same as or greater than magnitudes associated with prior tremulous movements, characteristics of a subsequent electric current to be applied to the body region may be adjusted.

12 Claims, 6 Drawing Sheets

(51) Int. Cl.
*A61B 5/00* (2006.01)
*A61N 1/02* (2006.01)
*A61N 1/08* (2006.01)
*A61B 5/389* (2021.01)

(52) U.S. Cl.
CPC .......... *A61B 5/389* (2021.01); *A61B 5/4836* (2013.01); *A61B 5/6824* (2013.01); *A61B 5/725* (2013.01); *A61B 5/7214* (2013.01); *A61N 1/025* (2013.01); *A61N 1/08* (2013.01); *A61N 1/36031* (2017.08); *A61B 5/6832* (2013.01); *A61B 2560/0204* (2013.01); *A61B 2562/0219* (2013.01); *A61B 2562/04* (2013.01); *A61N 1/36034* (2017.08)

(58) Field of Classification Search
USPC .......................................................... 607/48
See application file for complete search history.

(56) References Cited

U.S. PATENT DOCUMENTS

| | | | |
|---|---|---|---|
| 2013/0123568 A1* | 5/2013 | Hamilton | A61N 1/36017 600/13 |
| 2014/0078694 A1 | 3/2014 | Wissmar | |
| 2014/0257427 A1* | 9/2014 | Marnfeldt | A61N 1/36067 607/45 |
| 2014/0336722 A1* | 11/2014 | Rocon De Lima | A61N 1/36067 607/45 |
| 2015/0080674 A1 | 3/2015 | Drew et al. | |
| 2015/0102939 A1 | 4/2015 | Hong et al. | |
| 2015/0351690 A1* | 12/2015 | Toth | A61B 5/296 600/373 |
| 2016/0029958 A1 | 2/2016 | Le et al. | |
| 2016/0121110 A1 | 5/2016 | Kent et al. | |
| 2016/0228640 A1 | 8/2016 | Pindado et al. | |

* cited by examiner

METHODS AND SYSTEMS FOR TREMOR REDUCTION

CROSS-REFERENCE TO RELATED APPLICATIONS

This application is a divisional application of U.S. patent application Ser. No. 15/080,583 filed on Mar. 25, 2016 which is hereby incorporated by reference in its entirety.

BACKGROUND

Involuntary movement disorders of the human body cause impairment of proper motor function and result in a substantial decrease in quality of life, as well as various health problems. One such pathology, Essential Tremor (ET), is a neurodegenerative disease that causes an involuntary, tremulous movement which can affect almost any part of the body. Most often ET is presented in extremities of the body, such as the arms and hands, but ET can also be found in the head, voice, leg, and tongue, for example. ET is a kinetic tremor, often appearing during a movement of a body part, and is also a postural tremor, occurring when a subject maintains a position against gravity.

The cause of ET is currently unknown, rendering treatment of the disease more difficult. One treatment method is drug therapy, and the most common drugs used in such therapy are propanolol and pirimidone. Propanolol is a beta blocker that is used to treat hypertension and has numerous secondary effects that may include dizziness, difficulty sleeping, and nausea, among others. Pirimidone is an anticonvulsive that acts to decrease abnormal electrical activity on the brain and also has numerous secondary effects that may include somnolence and nausea, among others. Neither drug has shown to be efficient in reducing tremor amplitude.

Other treatment methods include brain operations such as thalamotomy and deep brain stimulation. Thalamotomy is the precise destruction of the thalamus, which controls involuntary movements. This type of surgery is expensive and is associated with a high risk of undesirable side effects. Deep brain stimulation is the implantation of electrodes in an area of the brain that controls involuntary movements, which are connected via cables to the chest of a patient.

SUMMARY

The present invention provides a novel a system and a method for reducing the amplitude of a tremor in a body of a subject. The system can advantageously decrease the amplitude of a tremor in a body region of a subject by at least 50% as compared to a non-treated body region of a subject. The inventors have found that unexpectedly, the amplitude of a tremor may be reduced by at least 70% and up to 100% (i.e., the amplitude is reduced fully.) In addition, the system of disclosure is portable, autonomous (i.e., no link to a computer or a cloud is needed) and self-regulating (i.e., by the algorithm that it uses.) As a result, the system of disclosure can easily be used by any subject who has ET.

In one embodiment, the method reduces the amplitude of a tremor in a body region of a subject, and includes transmitting electric current to a muscle of the subject that is associated with the tremor, receiving data indicating tremulous movements of the muscle, storing the received data, and determining, from the stored data, measurements associated with the tremulous movements. Measurements associated with a latest tremulous movement may then be compared to measurements associated with at least one prior tremulous movement, and responsively characteristics of the electric current may be changed if the measurements associated with the latest tremulous movement are the same as or greater than the measurements associated with the at least one previous tremulous movement.

In some example embodiments, a filter may be applied to remove selected data, such as a high pass filter or a low pass filter. The filtered data may then be stored and analyzed. Stored data may be removed that occurred prior to a threshold number of tremulous movements, or the data with the longest storage time may be removed after reaching a predetermined or set capacity of data. The data may be received from at least one sensor. The at least one sensor may comprise a motion sensor and/or an electromyogram.

The electric current may be transmitted via an electrode as a continuous wave train comprising a succession of waves with similar amplitudes at equal intervals, to the muscle. The regulation of the intensity of the wave amplitude may be automated. The intensity may be different and customized for each patient to account for a number of factors that affect the way current flows. Examples of such parameters are a patient's hydration level and temperature.

In one embodiment, the method of the disclosure may be used to treat a subject that has or is at risk for developing essential tremor disease. In another embodiment, the method of the disclosure may be used to diagnose or monitor treatment of essential tremor disease in a subject. The method of the disclosure may also be used to treat a subject that has or is at risk for developing other tremulous diseases, such as Parkinson's, for example.

In another embodiment, a tremor-reduction system is provided. The tremor-reduction system comprises a stimulation device configured to deliver electric current to a body region, at least one sensor, and a computing device comprising a processor and a non-transitory computer-readable medium configured to store program instructions thereon executable by the processor to cause the computing device to perform functions comprising: storing data received from the at least one sensor indicating movement of the body region, determining measurements associated with the stored data, comparing measurements associated with a latest movement of the body region to measurements associated with at least one prior movement of the body region, and responsively changing characteristics of the electric current if the measurements associated with the latest movement are not less than the measurements associated with the at least one previous movement.

DETAILED DESCRIPTION

The present disclosure provides methods and systems for reducing involuntary tremors in the human body.

Exemplary methods and systems are described herein. It should be understood that the word "exemplary" is used herein to mean "serving as an example, instance, or illustration." Any embodiment or feature described herein as "exemplary" or "illustrative" is not necessarily to be construed as preferred or advantageous over other embodiments or features. More generally, the embodiments described herein are not meant to be limiting. It will be readily understood that certain aspects of the disclosed methods systems and can be arranged and combined in a wide variety of different configurations, all of which are contemplated herein.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For the present application, the term "movement disorder" may mean an involuntary movement in a body region of a subject. A movement disorder may include a "tremulous movement" or a "tremor," for example, an involuntary trembling of the body or an extremity of the body, such as the limbs. The tremor may manifest as a rhythmic, involuntary muscular contraction. In some example embodiments, the movement disorder may be a kinetic and postural tremor such as ET. Such tremors may manifest within the range of about 4-8 Hz frequency.

The present application is directed to a method and system for reducing such tremors using electrical stimulation. Data received from sensors regarding muscle movement are stored and processed by a computing device, and responsively, changes in the electrical stimulation parameters can be made to reduce subsequent tremors.

Figure 1:
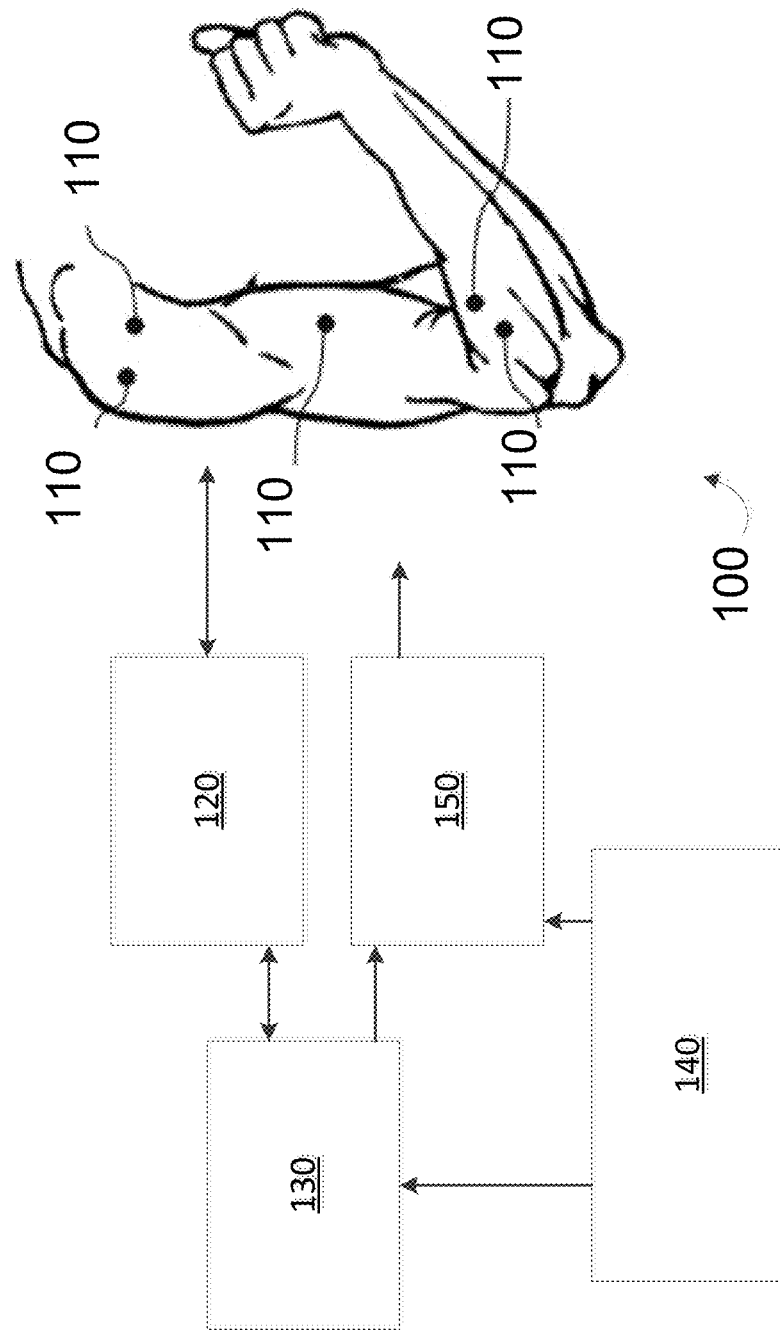
FIG. 1 depicts a schematic of an example tremor-reduction system in accordance with at least one embodiment.

FIG. 1 depicts a schematic of an example tremor-reduction system 100 in accordance with at least one embodiment. The system 100 may be used, among other things, to stimulate groups of muscles involved in movements that cause a tremor, and to record and process movement data to subsequently adjust the stimulation parameters.

The system 100 comprises electrodes 110, at least one sensor 120, a computing system 130, a power source 140, and a stimulation unit 150.

Electrodes 110 are connected to the stimulation unit 150, and are stimulation and recording electrode units, serving the dual purpose of stimulating different groups of antagonistic muscles, e.g., muscles involved in the movements that cause a tremor and recording tremor movements. The electrodes 110 may include an adhesive and conductive interface layer that directly interfaces with the skin surface and provides the electrical contact to conduct electrical energy to the muscle for effecting muscle contraction. Some benefits of the system 100 include the non-invasive placement of electrodes 110 as well as eliminating the possibility of the patient feeling tickle sensations or painful sensations, because the electrodes are placed over the muscles and not in a more invasive manner, such as to the nerves.

The groups of muscles sought to be stimulated by electrodes 110 may be muscles located on the upper extremities of a subject. Specifically, for example, the groups of muscles may be located on a forearm of a subject, and may comprise the pronator teres, large supinator (brachioradialis), biceps (large and short), deltoids, and rotator cuffs. In use, the electrodes 110 may be positioned in the muscles transcutaneously, for example, positioned so as to pass through or penetrate the skin, or may be non-invasive and simply placed on the surface of the skin without penetrating through the skin. The electrodes may be positioned in pairs over the skin for each muscle associated to a tremor. In one example embodiment, the electrodes may be placed a distance within the range of 0.5 to 8 cm from each other. In another example embodiment, the electrodes may be placed a distance within the range of 1 to 5 cm from each other. In yet another example embodiment, the electrodes may be placed a distance within the range of 1 to 8 cm, or 1 to 7 cm, or 1 to 6 cm, or 2 to 8 cm, or 2 to 7 cm, or 2 to 6 cm, or 2 to 5 cm, or 3 to 8 cm, or 3 to 7 cm, or 3 to 6 cm, or 3 to 5 cm, or 4 to 6 cm, or 4 to 5 cm from each other. In some example embodiments, only one pair of electrodes may be present. In other example embodiments, two or three pairs of electrodes may be present. Further, additional pairs of electrodes may be envisioned.

The at least one sensor 120 may include movement sensors and/or electromyogram sensors, and serve to monitor in real time the behavior of a tremor. The movement sensor may be located in or near a body region of a subject where a tremor has been detected. In one example embodiment, a movement sensor may be located on a subject's upper extremity. For example, the movement sensor may be located on an arm of a subject. More specifically, the movement sensor may be located on an extensor retinaculum, or a wrist, of a subject. The electromyogram sensor is directly connected to the electrodes 110 via wires. The at least one sensor 120 sends output concerning the behavior of the tremor to the computing system for further processing. The output may include data concerning amplitude and frequency of a tremor for a given time period, or for a given tremor event, a voltage, and data concerning motion such as angular and/or normal acceleration.

Figure 2:
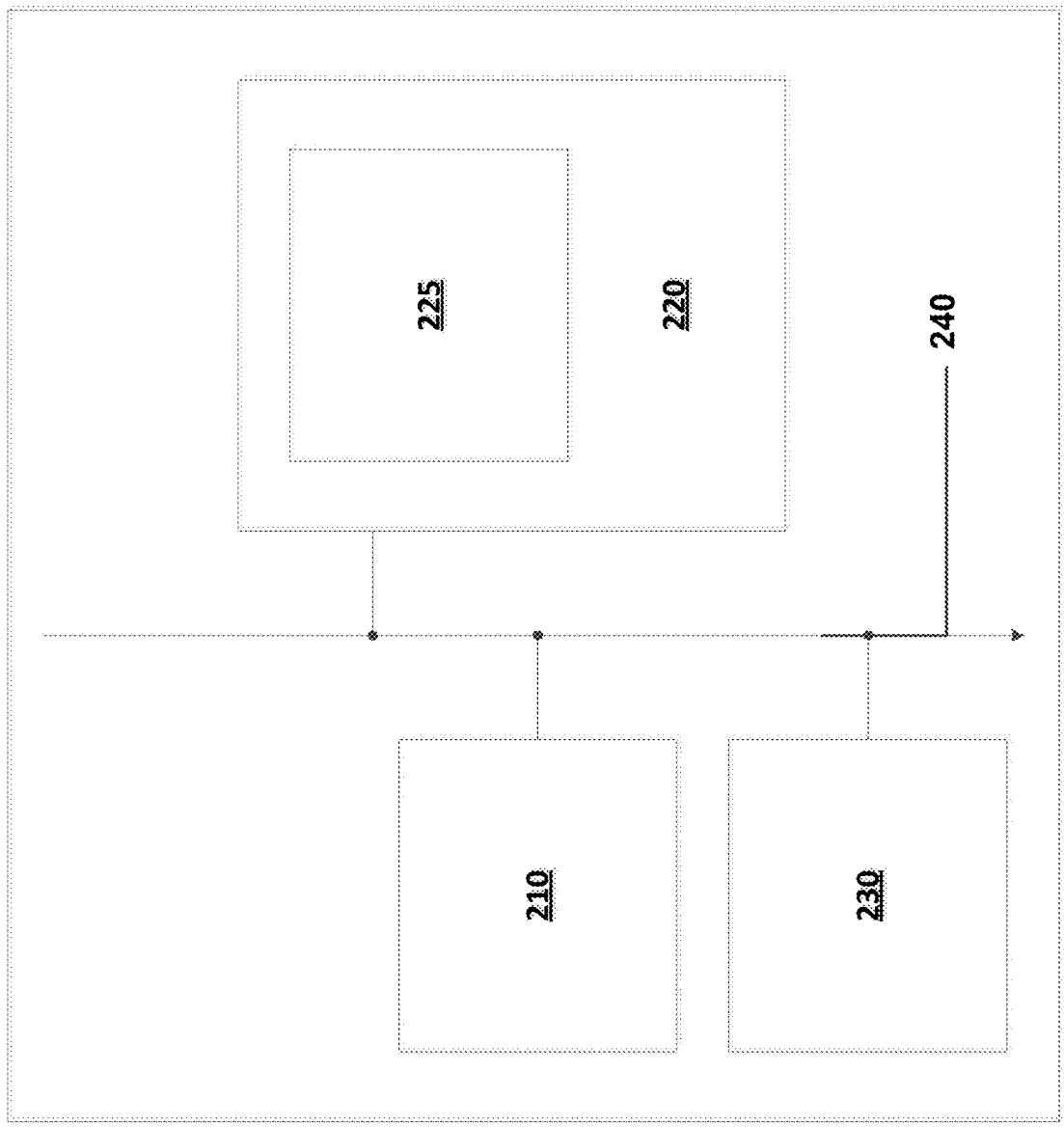
FIG. 2 depicts a functional block diagram illustrating an example computing system in accordance with at least one embodiment.

The computing system 130 may include a processor, data storage, and logic, discussed in further detail with respect to FIG. 2. In operation, the computing system 130 executes instructions to the stimulation unit 150 to stimulate the electrodes 110 present on a subject, and thereafter receives output from the one or more sensors 120 concerning movements of muscles of the subject. The output received may be stored within the data storage of the computing system 130. The processor is configured to perform an analysis on the stored data. In one example embodiment, the output is stored in a card such as microSD or SD. Stored output may be later evaluated for further medical diagnosis, prognosis, monitoring, and the like.

In one example embodiment, the system 100 may comprise two compartments, wherein one compartment houses the at least one sensor 120 and the other compartment houses the computing system 130 and stimulation unit 150, along with any associated electrodes 110. The two compartments may be connected via a cable or other wire, or may be wirelessly connected.

A filter may additionally be present in the system 100, and be applied to refine the data prior to analysis or processing by the computing system 130. For example, a filter can be applied to refine the data received by the computing system 130 such that only data from recent tremors are analyzed, with data from older tremors being discarded and removed from the data storage prior to data processing. As an example, a filter may be applied allowing only the last 100,000 data items to be analyzed. As another example, a filter may be applied allowing only the last 10,000 data items to be analyzed. In yet another example, a filter may be applied allowing at least the last 5,000 data items to be analyzed (thus not necessarily discarding data prior to the last 5,000 data items). The data may include voltages, accelerations, and other parameters or specific characteristics of the tremor output waves. The processor then analyzes the filtered data to determine the severity of a tremor by defining amplitude and frequency of a tremor output wave, and uses an algorithm, such as in the example method 400 discussed with reference to FIG. 4, to determine a preferred alternative to follow to reduce the tremor. An output interface is configured to transmit output from the computing system 130 to a display.

The power source 140 supplies energy to the computing system 130 and the stimulation unit 150. In one embodiment, the power unit or source 140 outputs one voltage that is supplied to both the computing system and the stimulation unit 150. The voltage may comprise a range between 3.3 volts (V) and 15V. In another example embodiment, the power source 140 may output two voltages: a first voltage that is supplied to the computing system and a second voltage that is supplied to the stimulation unit 150. In some example embodiments, the first voltage may comprise a range between 0V and 20V, between 3V and 10V, or between 3.3V and 5V. In some example embodiments, the second voltage may comprise a range between 0V and 15V, or between 1V and 15V, or between 2V and 15V, or between 3V and 15V, or between 0V and 12V, or between 1V and 12V, or between 2V and 12V, or between 3V and 12V, or between 0V and 10V, or between 1V and 10V, or between 2V and 10V, or between 3V and 10V, or between 0V and 9V, or between 1V and 9V, or between 2V and 9V, or between 3V and 9V, or between 3.3V and 9V. Still other ranges for the first voltage and the second voltage may be contemplated. The power source 140 may comprise one or more batteries, which may charge via a charger or Peltier plates.

The stimulation unit 150 serves to transmit a series of waves, via the electrodes 110, to a subject. The processor of the computing system 130 may execute instructions to the stimulation unit 150 to transmit waves at certain frequencies and amplitudes. In one example embodiment, a continuous wave train comprising variable frequency and amplitude is transmitted. The stimulation unit 150 may transmit voltages in the range of 10V to 120V (in some embodiments in the range of 10V to 110V, or 10V to 100V, or 10V to 90V, or 10V to 80V, or 10V to 70V, or 30V to 110V, or 30V to 100V, or 30V to 90V, or 30V to 80V, or 30V to 70V, or 40V to 110V, or 40V to 100V, or 40V to 90V, or 40V to 80V, or 40V to 70V).

In one example embodiment, the first voltage comprises a value within the range of 10V-90V, the electric current comprises a value that is less than 2 milliamps (mA), and the frequency is varied, without a specific threshold.

An algorithm process may be used to provide for adaptation to or customization for each user. First, the data provided by the at least one sensor 120 is saved in a buffer. The data then passes through adaptive filters to reduce the noise of false movements not caused by the tremulous movement. Next, the data passes through a cycle of repetitive checking to pre-evaluate tremor characteristics. This pre-evaluation includes comparing the spatial movements and calculating whether the displacement of the sensors corresponds to a spatial movement coherent to a bidimensional tremor. If the data comprising the spatial movements is coherent to a bidimensional tremor, the data is saved in data storage of the computing system 130 among or in association with the variables that are present in the system at the time of the tremor (e.g., frequency, voltage, battery state, and time since the first cycle began). In parallel, the state of the tremor is compared (the frequency and amplitude) with the average of the saved data. The average of the saved data comprises a variable quantity of previously obtained data. The comparison comprises extracting relative changes of the data values comprising the tremor. The relative changes may be classified as positive, negative, or non-variable. If the relative change is positive, the latest changes to the emission frequency are identified as "possible correct change." If the relative change is negative, the latest changes to the emission frequency are identified as "possible incorrect change." If, after a series of cycles, a pre-determined number of "possible correct change" outcomes exist, the system proceeds to change the values of emission of the variable (e.g., frequency, voltage, amplitude), subject to the emission falling within pre-determined security ranges. In one example embodiment, only one of the variables is changed per cycle.

Additionally, in parallel to the process described above, an additional cycle may conducted by a second processor to review the battery charge and how the charge affects the process discussed above, and a detection of changes may be made from inputs received from the user interface and the system status, helping to prevent errors on the outcoming wave.

FIG. 2 depicts a functional block diagram illustrating an example computing system 200, which may be the same as or similar to the computing system 100 of FIG. 1, in accordance with at least one embodiment. As shown, the computing system 200 comprises a processor 210, data storage 220 storing logic 225, and an output interface 230. The elements of the computing system 200 are shown coupled by a system bus or other mechanism 240. The computing system 200 may include elements instead of and/or in addition to those shown. For example, the computing system 200 may include two processors, as discussed above, that may operate in parallel.

Each of the processor 210, the data storage 220, the logic 225, and the output interface 230 are shown to be integrated within the computing system 200; however, the computing system 200 may, in some embodiments, comprise multiple devices among which the elements of the computing system 200 are distributed.

The processor may include one or more general purpose processors and/or dedicated processors, and may be configured to compute measurements of amplitude and frequency, as well as magnitudes of tremors, based on received data. The processor 210 may be configured to perform an analysis on various characteristics of a tremor so as to produce an output on the stored data. In one embodiment, the logic 220 may be executed by the processor 210 to perform such an analysis.

The output interface 230 may be configured to transmit the output to a display (not shown). To this end, the output interface 230 may be communicatively coupled to the display through a wired or wireless link. Upon receiving the output from the output interface 230, the display may display the output to a user.

Figure 3B:
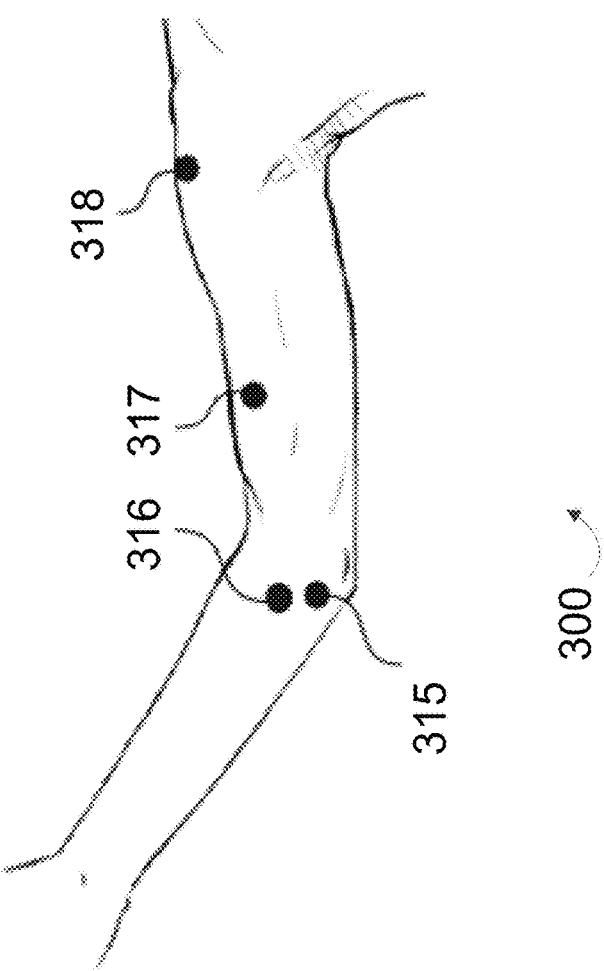
FIG. 3b depicts an example configuration for electrode placement in a body region of a subject in accordance with at least one embodiment.
Figure 3A:
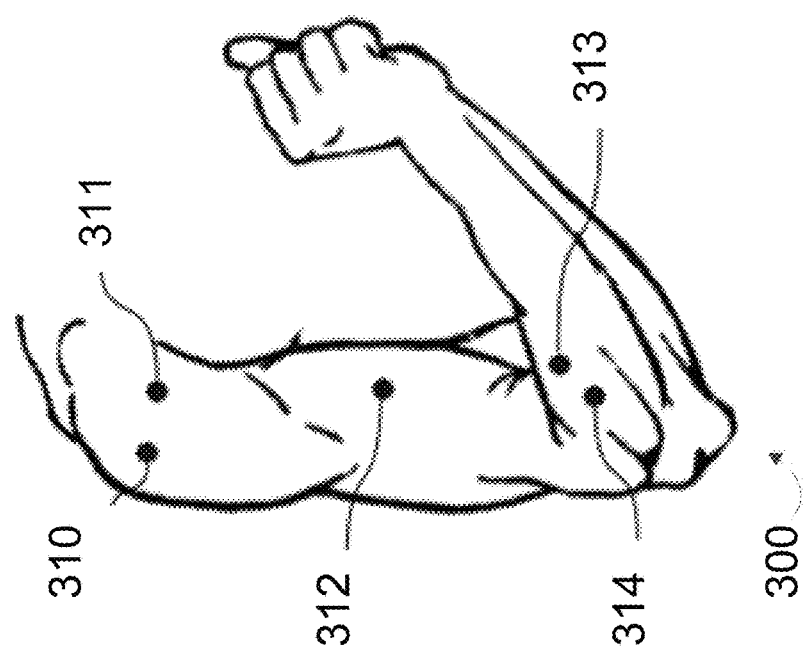
FIG. 3a depicts an example configuration for electrode placement in a body region of a subject in accordance with at least one embodiment.

FIGS. 3a and 3b depict an example setup for electrode placement in a body region 300 of a subject in accordance with at least one embodiment. The body region 300 depicted in FIGS. 3a and 3b is an upper extremity, namely, an arm of a subject, which is a common region for the manifestation of ET. As shown in FIG. 3a, electrodes 310, 311, 312, 313, and 314 are positioned along the length of the outside of the arm from the shoulder region to the forearm, and as shown in FIG. 3b, electrodes 315, 316, 317, and 318 are positioned along the length of the inside of the arm from the shoulder region to the forearm. Some groups of muscles that make up this region are the pronator teres, the large supinator, the biceps (large and short), and the deltoids.

Electrodes 310-318 may comprise stimulation and recording electrode units, and may be the same or similar to the electrodes 110 of FIG. 1. The connection between the electrodes is specific for each associated movement of the body region. For the example embodiment depicted in FIGS. 3a-3b, the combinations for connections between electrodes may include electrode 315 with electrode 316, electrode 313 with electrode 314, electrode 312 with electrode 317, or electrode 311 with electrode 310. Other example combinations for connections between electrodes may comprise electrode 315 with electrode 314, electrode 315 with electrode 313, electrode 316 with electrode 314, electrode 316 with electrode 313, or electrodes 315 or 316 with electrodes 314 and 313. Still other combinations for connections between electrodes may be envisioned.

Figure 3C:
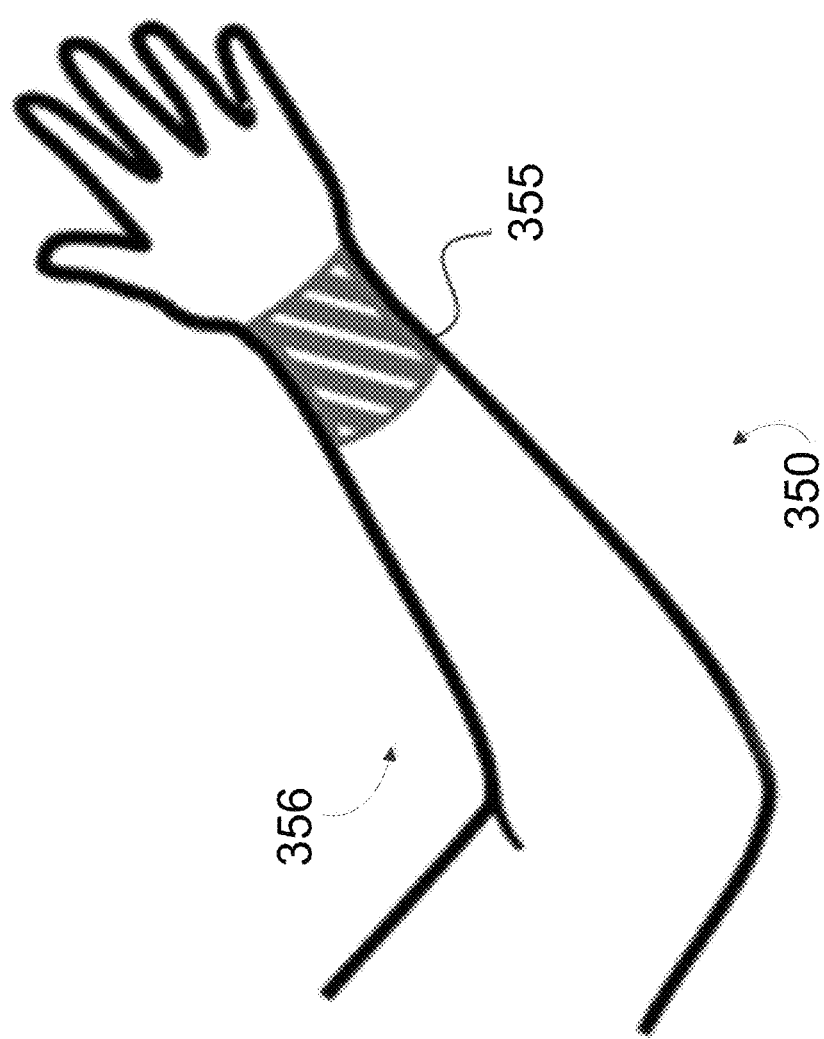
FIG. 3c depicts an example configuration for sensor placement in a body region of a subject in accordance with at least one embodiment.

FIG. 3c depicts an example setup for sensor placement in a body region 350 of a subject in accordance with at least one embodiment. FIG. 3c shows a movement sensor 355, which may be the same as or similar to the at least one sensor 120 of FIG. 1. The movement sensor 355 is shown located on an arm of a subject 356 where a tremor is detected. More specifically, the movement sensor 355 is shown on the extensor retinaculum of the arm. As discussed with reference to FIG. 1, an electromyogram may be additionally used as a sensing device, and may be directly connected to the electrodes.

Figure 4:
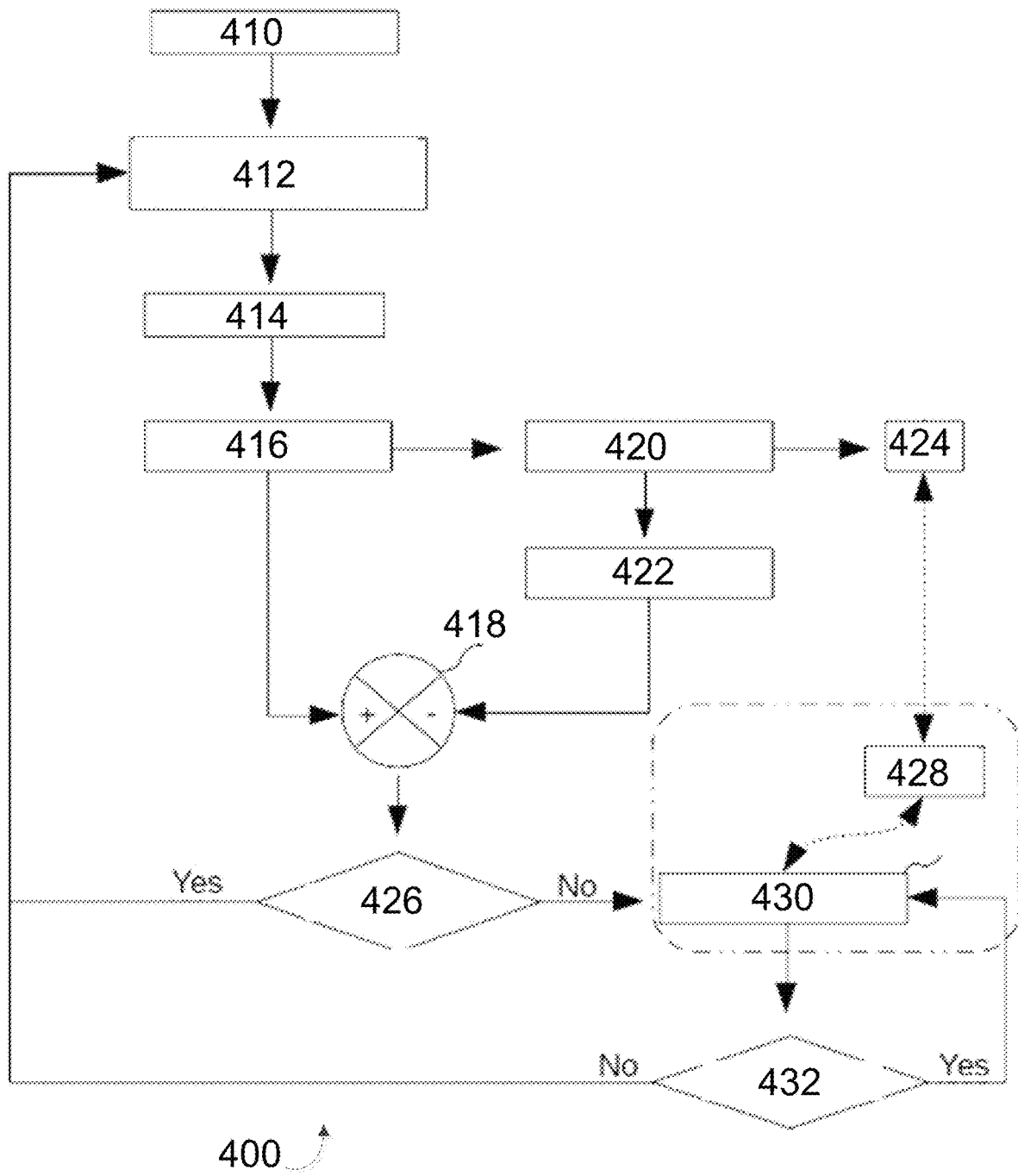
FIG. 4 depicts an example system algorithm for evaluation and processing of a tremor in a body region of a subject in accordance with at least one embodiment.

FIG. 4 depicts an example method 400 for evaluation and processing of a tremor in a body region of a subject in accordance with at least one embodiment. A processor, such as the processor 210 of the computing system 200, may execute instructions to apply the example method 400 to process a set of data received from one or more sensors. The method 400 may comprise one or more algorithms.

In operation, a cycle is initialized with a computing system, such as the computing systems 100 or 200, executing instructions to the stimulation unit to transmit electric current to a body region of a subject during a tremor, at block 410. Sensors, such as the sensors 120 of FIG. 1, obtain data from a body movement (e.g., a tremor), at block 412. The obtained data may then be sent through one or more filters, at block 414, which refines the data obtained from each sensor. The one or more filters may by high pass and/or low pass filters, designed to separate or eliminate noise from desired data. A real time state of the tremor is then determined, at block 416. The real time state may comprise information such as amplitude and frequency of the tremor, for example. In a first cycle, the stimulation unit sends pulses with specific characteristics that are provided by analysis of the data. Data that already passed through the one or more filters may be taken from the database may be analyzed and used to provide and update the specific characteristics. The specific characteristics may be updated and sent to the sensors in real time.

In subsequent cycles, the statistics, such as amplitude and frequency, for example, for the latest tremor are compared with the statistics for at least one previous tremor, at block 418. Additionally, the statistics for the latest tremor are stored in data storage, at block 420, for subsequent use. The stored data may either be used as the "last state," at block 422, in an analysis and comparison with the current or latest tremor state, or may be provided and stored in a database 424.

If there is no improvement on the tremor's stability after the analysis performed at block 418, the processor may change the characteristics or parameters of the emitted pulse. The algorithm may modify each isolated variable in order to find a stable level of tremor amplitude, at block 426, meaning that the magnitude of the latest tremor is less than a previous tremor. This process may be repeated for each variable. Example variables include frequency and voltage. The value representing the change for each variable, at block 428, is set by the analysis of the database. An additional step may be performed in the method 400 to verify that the characteristics of the output wave are within the security levels 432. The security levels represent a threshold level of pain for a subject. For example, if voltages in the range of 10V-20V are delivered to a subject, and the subject feels pain above 20V, 20V may be set as the security level not to be exceeded for that subject. The process represented by algorithm 400 may be repeated a number of times, with the data from each cycle being stored at block 420, thus delivering more values concerning how the tremor represents itself from different combinations of variables and contributing the values to the database 424. The database 424 may comprise, in some example embodiments, 100,000, 10,000, or 5,000 data items. Once the set capacity for the database 424 is reached, the oldest data may be eliminated, and the latest data added.

EXAMPLE EMBODIMENTS

The methods of the disclosure are illustrated further by the following examples, which are not to be construed as limiting the disclosure in scope or spirit to the specific procedures and systems described in them.

Figure 5A:
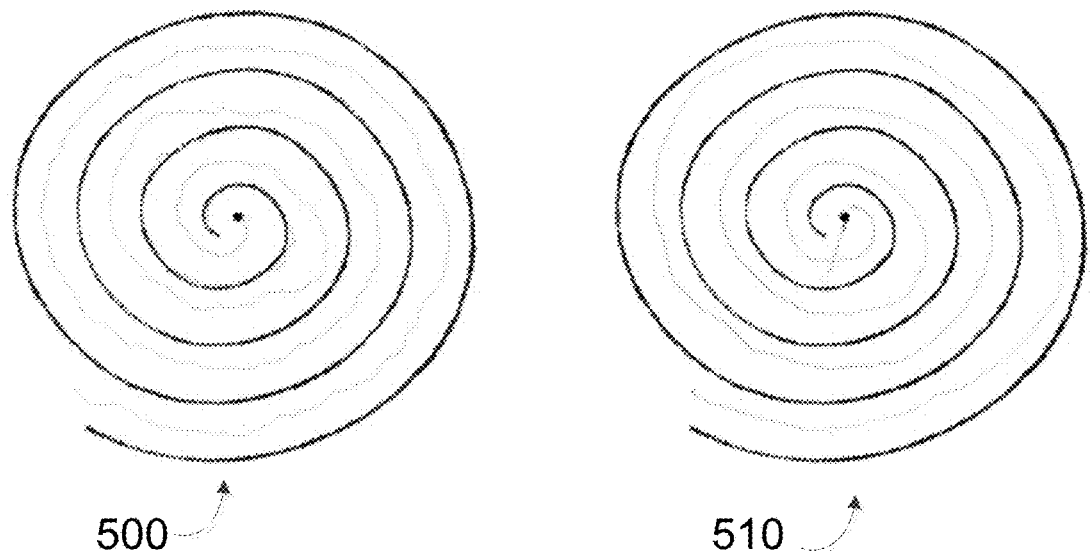
FIG. 5a depicts a test comparison of the example system of FIG. 1 in accordance with at least one embodiment.

FIG. 5a depicts a test comparison using a tremor-reduction system, such as the system 100 of FIG. 1, and a method, such as the method 400 of FIG. 4, in accordance with at least one embodiment. FIG. 5a depicts two swirls drawn by a subject with ET; the swirl 500 was drawn with the tremor-reduction system turned off, and the swirl 510 was drawn with the tremor-reduction system turned on.

Figure 5B:
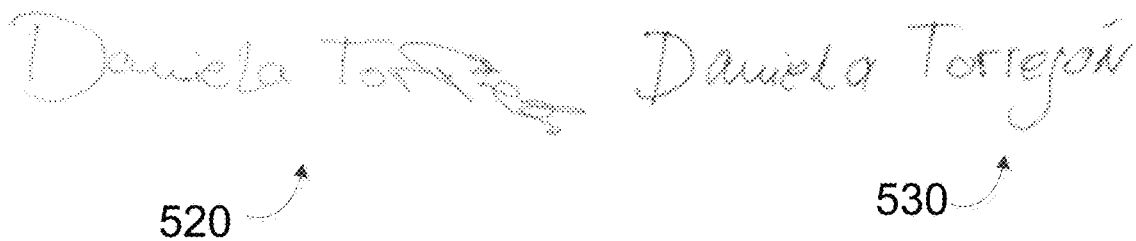
FIG. 5b depicts a test comparison of the example system of FIG. 1 in accordance with at least one embodiment.

FIG. 5b depicts a test comparison using a tremor-reduction system, such as the system 100 of FIG. 1, and a method, such as the method 400 of FIG. 4, in accordance with at least one embodiment. FIG. 5b shows two signatures drawn by a subject with ET; the signature 520 was written with the tremor-reduction system turned off, and the signature 530 was written with tremor-reduction system turned on.

Figure 5C:
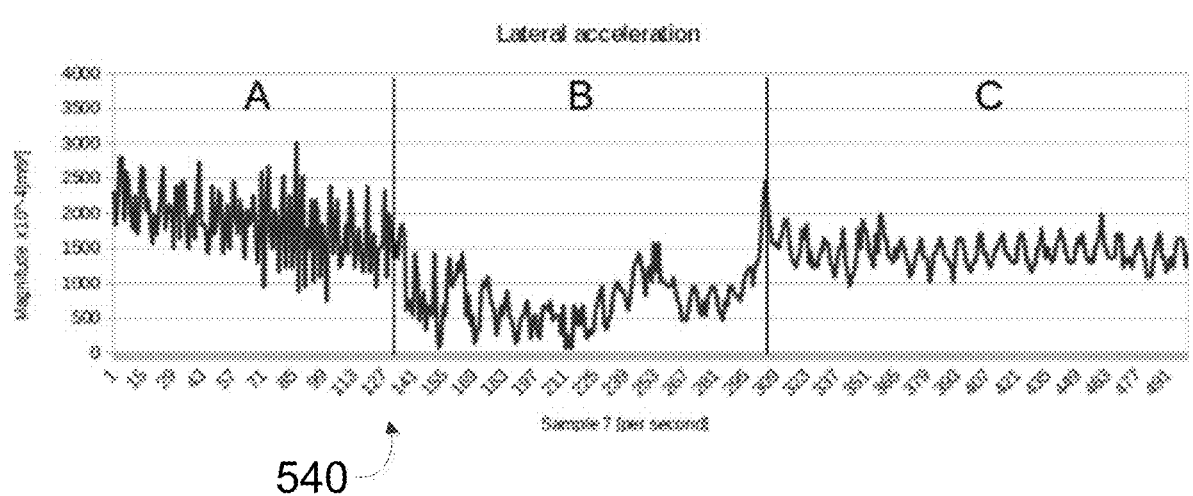
FIG. 5c depicts a graph plotting magnitude over lateral acceleration in an arm of a subject using the example system of FIG. 1, in accordance with at least one embodiment.

FIG. 5c depicts a graph 540 plotting magnitude over lateral acceleration in an arm of a subject, in accordance with at least one embodiment. The data shown in the graph 540 was obtained using a tremor-reduction system such as the system 100 of FIG. 1, and a method, such as the method 400 of FIG. 4.

In region A of graph 540, wherein the tremor-reduction system remains in an off state, a large variation in magnitude for tremors is shown. In region B, the tremor-reduction system is in an on state, and a method, such as the method 400 of FIG. 4, was used to search for stability. As shown in region B, the amplitude of the tremors decreased, but the tremors do not appear to be consistent in amplitude, and thus continue to appear to be unpredictable. In region C, however, the tremor-reduction system continues to be in an on state, and stability is finally reached. The magnitude of the tremors shown in region C is greatly reduced and predictable. Furthermore, muscle fatigue, muscle cramp, or other such secondary effects were not reported.

It is understood that the examples and embodiments described herein are for illustrative purposes only and that various modifications or changes in light thereof will be suggested to persons skilled in the art and are to be incorporated within the spirit and purview of this application and scope of the appended claims.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed:

1. A method for reducing severity of a tremor of a subject, comprising:
   executing instructions by a computing device to a stimulation device to transmit electric current to a muscle of the subject that is associated with the tremor;
   receiving, via the computing device, data indicating tremulous movements of the muscle;
   for data that is determined to be coherent to a bidimensional tremor, responsively storing the received data in the computing device, the stored data comprising measurements for at least one movement characteristic;
   comparing, via the computing device, measurements associated with a latest tremulous movement to an average measurement calculated from at least one prior tremulous movement of the muscle; and
   executing instructions by the computing device to responsively change characteristics of the electric current to be transmitted if the measurements associated with the latest tremulous movement are the same as or greater than the average measurement associated with the at least one prior tremulous movement of the muscle.

2. The method of claim 1, further comprising:
   executing instructions by the computing device to apply a filter to remove selected data.

3. The method of claim 2, further comprising:
   calculating, via the computing device, a frequency and an amplitude of a wave from the filtered data.

4. The method of claim 1, further comprising:
   after a predetermined data capacity is reached, the computing device removing a quantity of data with the longest storage time.

5. The method of claim 1, wherein the electric current is transmitted via an electrode located over the muscle.

6. The method of claim 1, wherein the data is received from at least one sensor.

7. The method of claim 6, wherein the at least one sensor comprises one or more of the following: (i) a motion sensor, and (ii) an electromyogram.

8. The method of claim 1, wherein executing instructions to transmit electric current further comprises executing instructions to transmit a continuous wave train via an electrode to the muscle.

9. The method of claim 1, wherein responsively changing characteristics of the electric current comprises changing the voltage of the electric current.

10. The method of claim 1, wherein responsively changing characteristics of the electric current comprises changing the frequency of the electric current.

11. The method of claim 1, wherein the subject has or is at risk for developing essential tremor disease, Parkinson's disease, or other involuntary movements.

12. The method of claim 1, which is used to diagnose or monitor treatment of essential tremor disease in the subject.

* * * * *